(12) United States Patent
Chandra

(10) Patent No.: US 6,562,378 B1
(45) Date of Patent: May 13, 2003

(54) NUTRITIONAL SUPPLEMENT FOR ADOLESCENTS

(75) Inventor: Renjit Kumar Chandra, Gurgaon (IN)

(73) Assignee: TSAR Health Private Ltd. (IN)

( * ) Notice: Subject to any disclaimer, the term of this patent is extended or adjusted under 35 U.S.C. 154(b) by 0 days.

(21) Appl. No.: 10/219,502

(22) Filed: Aug. 16, 2002

(51) Int. Cl.$^7$ .................. A61K 31/315; A61K 31/355; A61K 31/375; A61K 31/4188; A61K 31/4415; A61K 31/51; A61K 31/714; A61K 33/00; A61K 33/04; A61K 33/06; A61K 33/16; A61K 33/18; A61K 33/24; A61K 33/26; A61K 33/30; A61K 33/32; A61K 31/07; A61K 31/095; A61K 31/28; A61K 31/295; A61K 31/30

(52) U.S. Cl. .................. 424/601; 426/74; 426/800; 426/73; 514/52; 514/75; 514/167; 514/168; 514/184; 514/249; 514/251; 514/276; 514/345; 514/356; 514/387; 514/458; 514/474; 514/492; 514/494; 514/499; 514/500; 514/502; 514/505; 514/563; 514/725; 514/763; 514/885; 514/904; 514/905; 424/600; 424/602; 424/603; 424/604; 424/605; 424/606; 424/630; 424/631; 424/632; 424/633; 424/634; 424/635; 424/637; 424/638; 424/639; 424/640; 424/641; 424/643; 424/646; 424/647; 424/648; 424/655; 424/656; 424/667; 424/668; 424/669; 424/670; 424/671; 424/672; 424/673; 424/674; 424/675; 424/676; 424/678; 424/681; 424/682; 424/683; 424/686; 424/687; 424/688; 424/689; 424/692; 424/693; 424/694; 424/695; 424/696; 424/697; 424/702; 424/722

(58) Field of Search .................. 424/600–606, 424/630–635, 637–641, 643, 646–648, 655–656, 667–676, 678, 681–683, 686–689, 692–697, 702, 722; 514/52, 75, 167, 168, 184, 249, 251, 276, 345, 356, 387, 458, 474, 492, 494, 499, 500, 502, 505, 563, 725, 763, 885, 904, 905; 426/73, 74, 800

(56) References Cited

U.S. PATENT DOCUMENTS

| | | | |
|---|---|---|---|
| 4,070,488 A | 1/1978 | Davis | 426/72 |
| 4,237,118 A | 12/1980 | Howard | 424/630 |
| 4,994,283 A | 2/1991 | Mehansho et al. | 426/74 |
| 5,556,644 A | 9/1996 | Chandra | 424/630 |
| 5,561,160 A * | 10/1996 | Walaszek et al. | 514/574 |
| 5,571,441 A * | 11/1996 | Andon et al. | 252/1 |
| 5,719,133 A | 2/1998 | Schmidl et al. | 514/58 |
| 5,719,134 A | 2/1998 | Schmidl et al. | 514/58 |
| 5,770,215 A * | 6/1998 | Moshyedi | 424/440 |
| 5,780,039 A * | 7/1998 | Greenberg et al. | 424/400 |
| 5,869,084 A | 2/1999 | Paradissis et al. | 424/439 |
| 5,922,704 A | 7/1999 | Bland | 514/185 |
| 5,925,377 A | 7/1999 | Gerth et al. | 424/451 |
| 6,245,360 B1 | 6/2001 | Markowitz | 424/641 |
| 6,299,896 B1 | 10/2001 | Cooper et al. | 424/441 |
| 6,361,800 B1 | 3/2002 | Cooper et al. | 424/630 |
| 6,451,341 B1 * | 9/2002 | Slaga et al. | 424/468 |
| 2002/0015761 A1 * | 2/2002 | Prosise et al. | 426/72 |
| 2002/0102330 A1 * | 8/2002 | Schramm et al. | 426/72 |

FOREIGN PATENT DOCUMENTS

| | | | |
|---|---|---|---|
| WO | 99/58000 | * | 11/1999 |
| WO | 01/68534 | * | 9/2001 |

OTHER PUBLICATIONS

Torkos, S. Choosing a vitamin and Mineral Supplement for Your Child [retrieved on Dec. 27, 2002]. Retrieved from the Internet: <URL: www.thrillworks.com/health_notes/Supp/Multi_vitamin.htm.*

Centrum Junior product information [retrieved on Dec. 27, 2002]. Retrieved from the Internet: <URL: http://www.centrum.co.uk/content–28.*

Sesame Street Complete Product Information [retrieved on Dec. 27, 2002]. Retrieved from the Internet: <URL: http://www.rxsolutions.com.*

Flinstones Complete Product Information [retrieved on Dec. 27, 2002]. Retrieved from the Internet: <URL: http://www.bayercare.com.*

Bugs Bunny Tablets Plus Iron product Information [retrieved on Dec. 27, 2002]. Retrieved from the Internet: <URL: http://www.otcservice.com/productpages/BugsBunnyVitamins.*

CNN.com—Cite: Health/Diet/Fitness: Article entitled "New guidelines released on vitamin, mineral supplements" 2 pages; Jan. 9, 2001.

Alternate Health.com—Article entitled "Vitamin/Mineral Supplements" 3 pages; Aug. 12, 2002.

* cited by examiner

Primary Examiner—John Pak
(74) Attorney, Agent, or Firm—Liniak, Berenato & White

(57) ABSTRACT

A multinutrient nutritional supplement is provided that is designed to be most effective in optimizing health, increasing the immunity and decreasing the instances and severity of infection particularly among adolescents.

5 Claims, 2 Drawing Sheets

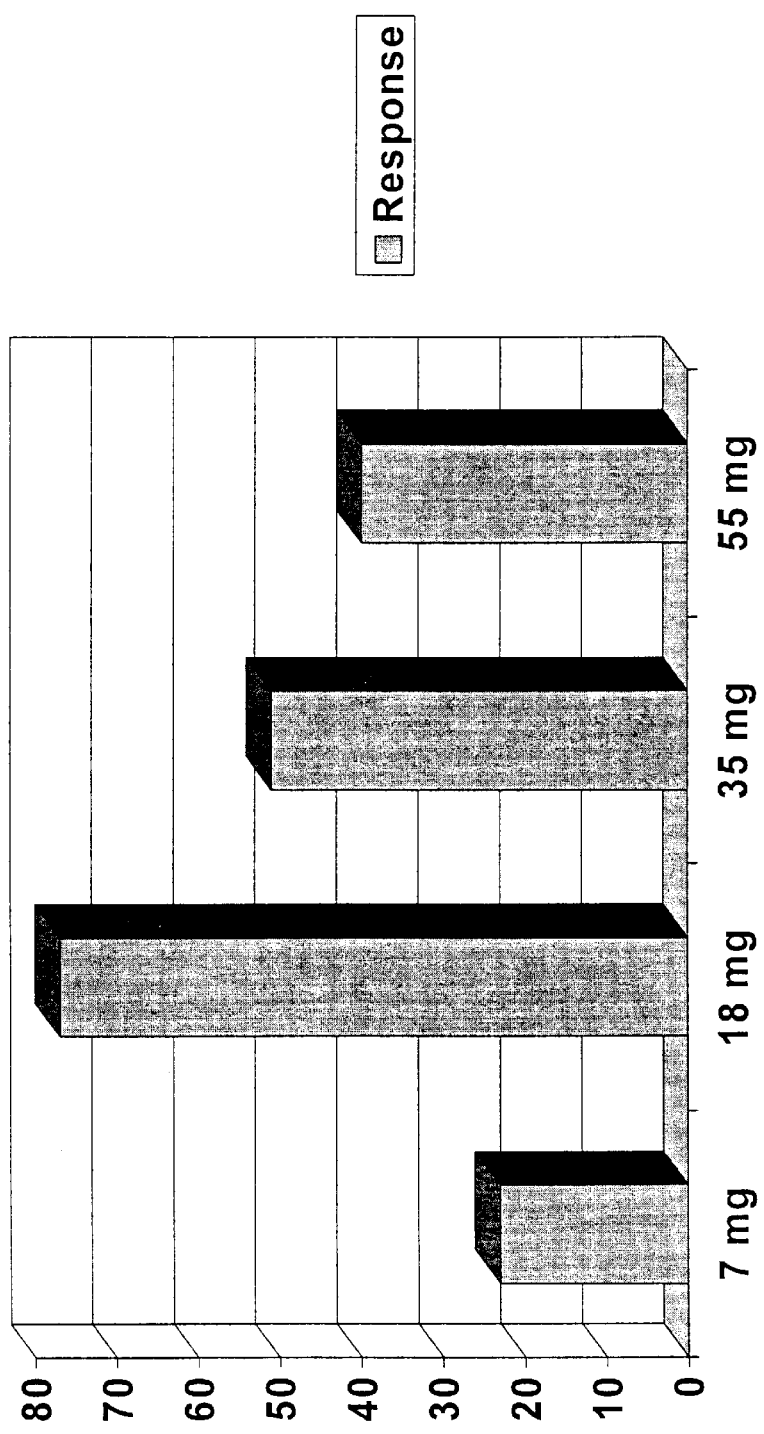
Fig. 1. Lymphocyte response to mitogen PHA related to zinc intake

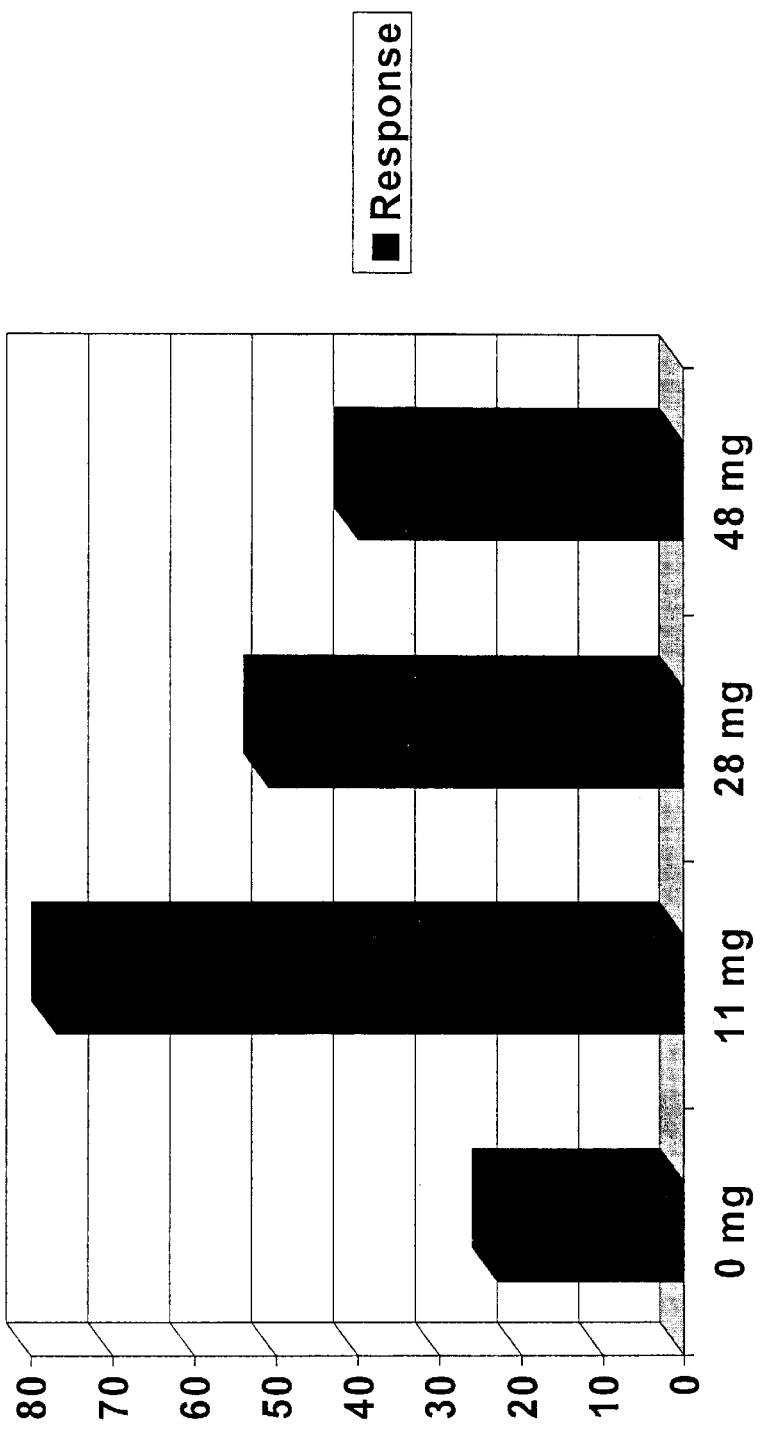
Fig. 2. Lymphocyte response to mitogen PHA related to amount of zinc supplement in 13-18 years old adolescents

NUTRITIONAL SUPPLEMENT FOR ADOLESCENTS

FIELD OF THE INVENTION

The present invention relates to nutritional supplements, and more particularly relates to nutritional supplements optimized for administration to adolescents. The invention further relates to nutritional supplements optimized for enhanced immunological response in adolescents.

BACKGROUND OF THE INVENTION

The common concept of malnutrition comes from our exposure to the print, radio, and television media showing pictures and relating stories of the horrors of severely wasted young children in low poor countries of the world, in refugee camps, and in areas affected by wars and natural disorders such as drought, famine and floods.

Although nutrient deficiencies that result in malnutrition are severe and frequent in adolescents in lesser-developed countries and in developing countries, they also often occur in adolescents even in affluent countries such as the United States, Canada, Western Europe, Japan and elsewhere. Other than the elderly in whom nutritional problems are common, adolescents are the second group most affected by nutritional deficiencies in the USA, Canada, Western Europe and other industrialized countries. For example, iron deficiency documented by appropriate blood tests is observed in as many as 20–28% of the teenagers in these countries. The prevalence of iron deficiency is higher is girls than in boys. Other nutrients found to be deficient in a proportion of adolescents are beta-carotene, vitamin C, vitamin D, vitamin E, vitamins B6, folic acid, and zinc. In the poor nations of Asia, Africa and South America, the problem is much more frequent and severe. For instance, in most parts of rural India, iron deficiency is observed in as many as 60 to 80% of boys and girls respectively. Other nutrient deficiencies are also common. There is a paucity of comprehensive and complete data for many nutrients.

These nutrient losses and deficiencies most often occur due to lifestyle factors and inadequate dietary patterns. Among other outcomes, infection is a consequence of such nutrient deficiencies, largely because malnutrition reduces immune responses.

Diets complete in nutritional substances are important for the human body in order to afford consistent high levels of optimum performance, both in cognitive ability and physical health. Although the exact needs of the human species to develop and maintain peak performance on a daily basis and sustain such performance for the various stages and throughout the duration of the human life are not completely understood, it is widely recognized that maintaining balanced nutrition coupled with sensible levels of daily exercise are the fundamental bases for optimizing the condition of the human body. It is also widely accepted that the risk of many common ailments from environmental sources or many ailments arising from genetic consequences can be reduced through the daily practice of, in addition to exercise, a complete nutritional regime fortified with certain vitamins, minerals, and the like. Increased human longevity and health is understood to be a potential consequence of these daily practices.

Vitamin and mineral preparations are also commonly administered to treat specific medical conditions, including malnutrition, or as general nutritional supplements. Studies have elucidated the important physiological roles played by vitamins and minerals, and established a correlation between deficiencies or excesses of these nutrients and the etiologies of certain disease states in humans.

It has further become recognized that various groups of the human population require different quantities and types of vitamins and minerals to prevent or alleviate diseases, as well as to maintain general good health. Much of the prior art has focused on the needs of pregnant women, particularly their need for increased iron and calcium such as that shown in U.S. Pat. No. 4,994,283, directed to nutritional mineral supplements which include iron and calcium compounds in combination with citrates or tartrates, ascorbates, and fructose in an effort to reduce the tendency of calcium to inhibit the bioavailability of iron, so that the conjoint bioavailability of these two minerals is enhanced.

The special nutritional needs of the elderly have been previously addressed in my prior U.S. Pat. No. 5,556,644 in which a multinutrient nutritional supplement was provided that was designed to be most effective in increasing the immunity and decreasing the instances and severity of infection particularly among older persons.

Efforts to address the nutritional needs of children of ages 1 to 10, such as shown in U.S. Pat. Nos. 5,719,133 and 5,719,134, have focused enteral food compositions for children between the ages of 1 and 10 having various diseases where the enteral food compositions have a the amino acid, mineral and carbohydrate profile modified to reflect the needs of children of ages 1 to 10. Such compositions are not for oral administration, and are not directed to optimizing the health of normal children and children in need of nutritional supplementation to enhance immune response and to avoid the problems of malnutrition. Furthermore, such supplements are not directed to adolescents of 13–18 years of age and their special needs.

SUMMARY OF THE INVENTION

The present invention overcomes the shortcomings of known unitary vitamin and mineral containing nutritional supplements by providing multi-vitamin and mineral nutritional supplements which are specifically tailored for administration to adolescents and provides a method for maintaining the optimal health and immunological function of adolescents by administration of the same. The formulations of the invention have been found to maximize the benefit of vitamin and mineral supplementation for adolescents, while concurrently minimizing the undesirable side effects characteristic of known nutritional supplements.

The compositions of the invention include certain essential nutritional components in dosage levels which have been found to optimize development of adolescents and maintain their health, as well as to maximize their immunological function.

Thus, the invention provides a multi-vitamin and mineral supplement for administration to adolescents, which comprises calcium in the amount of about 425 to about 575 mg; chromium in the amount of about 42.5 to about 57.5 µg; copper in the amount of about 391 to about 529 µg; fluoride in the amount of about 1.53 to about 2.07 mg; iodine in the amount of about 85 to about 115 µg; iron in the amount of about 23.8 to about 32.2 mg; magnesium in the amount of about 42.5 to about 57.5 mg; manganese in the amount of about 2.65 to about 3.45 mg; molybdenum in the amount of about 34 to about 46 µg; phosphorus in the amount of about 425 to about 575 mg; selenium in the amount of about 123.25 to about 166.75 µg; zinc in the amount of about 9.35 to about 12.65 mg; beta-carotene in the amount of about 2.04 to about 2.76 mg; vitamin A in the amount of about 637.5 to about 862.5 µg; vitamin C in the amount of about 63.75 to about 86.25 mg; vitamin D in the amount of about 9.35 to about 12.65 µg; vitamin E in the amount of about 18.7 to about 25.3 mg; thiamin in the amount of about 3.65 to about 4.95 mg; riboflavin in the amount of about 3.23 to about 4.37 mg; niacin in the amount of about 16.15 to about 21.85 mg; vitamin B6 in the amount of about 2.46 to about 3.34 mg; folate in the amount of about 340 to about 460 µg; vitamin B12 in the amount of about 3.99 to about 5.41 µg; pantothenic acid in the amount of about 1.7 to about 2.3 mg; and biotin in the amount of about 17 to about 23 µg.

An advantage of the present invention is that the adolescent nutritional supplement supplies the right amount of the necessary nutrients including vitamins and minerals to adolescents to assure optimal intake of nutrients needed for health and maximal immunological response and protection against nutritional losses and deficiencies due to lifestyle factors and inadequate dietary patterns.

Another advantage of the present invention is that the adolescent nutritional supplement provides the necessary vitamins and minerals to allow adolescents using the supplement to maintain their present health and positively influence their future health.

Another advantage of the present invention is that the adolescent nutritional supplement increases and/or optimizes the immunological responses of adolescent users including lymphocyte response to PHA, interleukin-2, antibody response and thymulin activity.

Still another advantage of the present invention is that the adolescent nutritional supplement reduces the occurrence of common infections in the adolescent users.

These and other advantages and benefits of the present invention will be apparent to those skilled in the art upon reading and understanding the following detailed description of the invention.

BRIEF DESCRIPTION OF THE DRAWINGS

FIG. 1 is a dose response curve for the total amount of zinc taken by 13 to 18 year old adolescents; and FIG. 2 is the dose response curve for zinc as administered to 13 to 18 year old adolescents with the amounts of zinc given as a supplement shown.

DETAILED DESCRIPTION OF THE PREFERRED EMBODIMENTS

The present invention is directed to a nutritional supplement containing the appropriate amounts of vitamins and trace elements that sustains an optimum level of immunity and reduces the incidence of infections among 13–18 year old boys and girls. As noted above, none of the nutrient preparations in the market have documented benefits shown by this invention.

The present invention is directed to a nutritional supplement for administration to adolescents to enhance and improve their immunological response which comprises calcium in the amount of about 425 to about 575 mg; chromium in the amount of about 42.5 to about 57.5 µg; copper in the amount of about 391 to about 529 µg; fluoride in the amount of about 1.53 to about 2.07 mg; iodine in the amount of about 85 to about 115 µg; iron in the amount of about 23.8 to about 32.2 mg; magnesium in the amount of about 42.5 to about 57.5 mg; manganese in the amount of about 2.65 to about 3.45 mg; molybdenum in the amount of about 34 to about 46 µg; phosphorus in the amount of about 425 to about 575 mg; selenium in the amount of about 123.25 to about 166.75 µg; zinc in the amount of about 9.35 to about 12.65 mg; beta-carotene in the amount of about 2.04 to about 2.76 mg; vitamin A in the amount of about 637.5 to about 862.5 µg; vitamin C in the amount of about 63.75 to about 86.25 mg; vitamin D in the amount of about 9.35 to about 12.65 µg; vitamin E in the amount of about 18.7 to about 25.3 mg; thiamin in the amount of about 3.65 to about 4.95 mg; riboflavin in the amount of about 3.23 to about 4.37 mg; niacin in the amount of about 16.15 to about 21.85 mg; vitamin B6 in the amount of about 2.46 to about 3.34 mg; folate in the amount of about 340 to about 460 µg; vitamin B12 in the amount of about 3.99 to about 5.41 µg; pantothenic acid in the amount of about 1.7 to about 2.3 mg; and biotin in the amount of about 17 to about 23 µg.

The adolescent nutritional supplement of the present invention is more particularly directed to a supplement comprising calcium in the amount of about 500 mg; chromium in the amount of about 50 µg; copper in the amount of about 460 µg; fluoride in the amount of about 1.8 mg; iodine in the amount of about 100 µg; iron in the amount of about 28 mg; magnesium in the amount of about 50 mg; manganese in the amount of about 3 mg; molybdenum in the amount of about 40 µg; phosphorus in the amount of about 500 mg; selenium in the amount of about 145 µg; zinc in the amount of about 11 mg; beta-carotene in the amount of about 2.4 mg; vitamin A in the amount of about 750 µg; vitamin C in the amount of about 75 mg; vitamin D in the amount of about 11 µg (44 IU); vitamin E in the amount of about 22 mg; thiamin in the amount of about 4.3 mg; riboflavin in the amount of about 3.8 mg; niacin in the amount of about 19 mg; vitamin B6 in the amount of about 2.9 mg; folate in the amount of about 400 µg; vitamin B12 in the amount of about 4.7 µg; Pantothenic acid in the amount of about 2.0 mg; and biotin in the amount of about 20 µg.

Each of the component vitamins and minerals making up the nutritional supplement of the present invention are preferably provided in bioavailable forms. This means that absorption and utilization are enhanced. As a result, more of the nutrients provided will actually be available to the adolescent user, rather than simply passing through the digestive track unused by the body. However, other forms of the components may be used if the amounts of each component are adjusted to give similar bioavailable quantities.

Calcium

Calcium is the most common mineral in the human body and is vitally important because adequate intakes are an important determinant of bone health and risk of fracture or osteoporosis. Calcium has four major biological functions: 1) structural as stores in the skeleton, 2) electrophysiological—carries charge during an action potential across membranes, 3) intracellular regulator, and 4) as a cofactor for extracellular enzymes and regulatory proteins. Although acute deficiency symptoms are avoided because of the large skeletal stores, prolonged bone resorption from chronic dietary deficiency can lead later in life to osteoporosis due to inadequate accumulation of bone mass during growth in adolescence. Dietary calcium deficiency also has been associated with increased risk of hypertension, preeclampsia, and colon cancer. Increasing calcium intakes during adolescence increases calcium accretion up to 1300 mg/day and increases bone mineral content. Even in children, bone density determines fracture risk.

Chromium

Chromium is an essential nutrient required for normal sugar and fat metabolism and functions primarily by potentiating the action of insulin. Signs of deficiency include impaired glucose tolerance and elevated circulating insulin. In some studies, chromium supplementation has reduced total serum cholesterol, triglycerides and apolipoprotein B and increased HDL-cholesterol.

Copper

Copper is an essential trace element involved in the absorption, storage and metabolism of iron. Copper deficiency is often observed in those suffering from malnutrition and can result in anemia, cardiac abnormalities such as blood vessel and heart rupture, abnormal EKG's and elevated levels of serum cholesterol, triglycerides and glucose. A lifetime of marginal diet copper is thought to lead to heart disease.

Copper helps keep blood vessels elastic, is needed for the formation of elastin and collagen, functions as an iron oxidizer, and is needed for the proper functioning of vitamin C. In a preferred embodiment of the invention, copper is dosed in a pharmaceutically acceptable copper compound including, but not limited to, cupric oxide, cupric sulfate, cupric gluconate, and combinations thereof.

Fluoride

Fluoride's best known effect is to serve as a catalyst for both the mineralization of developing tooth enamel prior to tooth eruption and for remineralization of surface enamel, thus greatly reducing occurrence of dental decay. Fluoride may also assist in stimulating new bone growth. Most foods are very low in fluoride and thus the major source of fluoride is fluoridated drinking water.

Iodine

Iodine forms an essential component of the thyroid hormones which regulate cell activity and growth in virtually all tissues and are, therefore, essential for both normal growth and development. Iodine deficiency impairs growth and neurological development, which can damage the brain and can lead to a wide spectrum of health problems, ranging from mild intellectual impairment to severe mental retardation, growth stunting, apathy, and impaired movement, speech or hearing. Cretinism is a rare disorder in which many of these abnormalities occur, represents the extreme of early iodine deficiency. Much more widespread is an intellectual blunting that may afflict as many as 50 million of the estimated 1.6 billion "at-risk" people living in iodine deficient regions, making iodine deficiency the most common preventable cause of mental retardation in the world. Because of decreased production of thyroid hormones, iodine deficiency causes compensatory hypertrophy of the thyroid gland as it attempts to make more thyroid hormone, resulting in a goiter—a disfiguring condition that is common in high-risk areas. Collectively, health problems arising from a lack of iodine are known as iodine deficiency disorders (IDD).

Iron

Iron is an essential nutrient that carries oxygen and forms part of the oxygen-carrying proteins, hemoglobin in red blood cells and myoglobin in muscle. It is also a necessary component of various enzymes. Iron deficiencies result in anemia.

Any pharmaceutically acceptable iron compound can be used in the nutritional supplement of the present invention and may be chosen from any of the well-known iron II (ferrous) or iron III (ferric) supplements, such as ferrous sulfate, ferric chloride, ferrous gluconate, ferrous lactate, ferrous tartrate, iron-sugar-carboxylate complexes, ferrous fumarate, ferrous succinate, ferrous glutamate, ferrous citrate, ferrous pyrophosphate, ferrous cholinisocitrate, ferrous carbonate, and the like.

In a further embodiment of the present invention, the iron compound comprises a pharmaceutically acceptable ferrous sulfate compound coated with a pharmaceutically acceptable film forming material which permits release of the ferrous sulfate in the intestine of the adolescent administered the supplement. Suitable coatings include any material known in the art for forming enteric, controlled release, or sustained release coatings, such as cellulose ethers including hydroxypropyl methylcellulose, methylcellulose, ethylcellulose, and carboxymethylcellulose; cellulose esters such as cellulose acetate, cellulose acetate phthalate, and cellulose nitrate; acrylate and methacrylate copolymers; and the like. The coated iron compound has been found to provide increased iron bioavailability by minimizing interaction between the iron compound and divalent cations such as calcium in the nutritional supplement. In addition, the coated iron compound is better tolerated and causes few stomach problems.

Magnesium

Any pharmaceutically acceptable magnesium compound can be used.

Manganese

Manganese is important to maintain the integrity of the skin, bone and menstrual cycle, and in cholesterol metabolism.

Molybdenum

Molybdenum is an essential nutrient that is a component of a number of enzymes involved in the metabolic process.

Phosphorus

Phosphorus is an essential mineral that is found in all cells within the body. The metabolism of all major metabolic substrates depends on the functioning of phosphorus as a cofactor in a variety of enzymes and as the principal reservoir for metabolic energy.

Selenium

Selenium is an essential trace element that functions as a component of enzymes involved in antioxidant protection and thyroid hormone metabolism. Characteristic signs of selenium deficiency have not been described in humans, but very low selenium status is a factor in the etiologies of a juvenile cardiomyopathy (Keshan Disease) and a chondrodystrophy (Kashin-Beck Disease) that occur in selenium-deficient regions of China.

Zinc

Zinc is required for proper formation of DNA and RNA and is needed for growth and sexual development of women.

Beta-carotene

Beta-carotene is a precursor to vitamin A and is associated with decreased risk of some degenerative diseases, and there is some evidence also for its role in improving immune function. Deficiencies may be associated with detrimental but non-life-threatening skin changes (including acne and dermatitis).

Vitamin A

Vitamin A is a fat-soluble vitamin. The best-known function of vitamin A is in vision, where it participates in the visual cycle. Night blindness is one of the early signs of vitamin A deficiency, because of the role of vitamin A in vision. Bacterial invasion and permanent scarring of the cornea of the eye (xerophthalmia) is a symptom of more profound deficiency. Profound vitamin A deficiency also results in altered appearance and function of skin, lung, and intestinal tissues. Children are most at risk of vitamin A deficiency because they have not yet developed adequate vitamin A stores. It has been estimated that 5 million children in the world become blind each year, 70% of these due to vitamin A deficiency. Over half of these blind children die from malnutrition and associated illnesses.

Vitamin C

Vitamin C, also known as ascorbic acid, is necessary for the synthesis of collagen and is used as an antioxidant. Vitamin C fights infection, reduces inflammation, heals wounds, reduces the risk of heart disease, lowers cholesterol, reduces the risk of lung, stomach, and esophageal cancers, reduces cervical epithelial abnormalities, inhibits N-nitrosamine, and reduces the severity of colds.

Vitamin D

Vitamin D assists in the mineralization and calcification of bone, prevents rickets in children, prevents osteomalacia in adults, preserves bone and tooth growth, and lowers blood pressure. Vitamin D is fat-soluble.

Vitamin E

Vitamin E is also fat-soluble and is needed for the maintenance of cell membranes and for neurological health. Vitamin E is the generic term for a group of related substances which include alpha-tocopherol, beta-tocopherol, gamma-tocopherol, and delta-tocopherol. In addition, each of these four compounds has a "d" form, which is the natural form, and a "dl" form which is the synthetic form.

Thiamin

Thiamin (vitamin B-1) is a water-soluble substance, consisting of thiazole and pyrimidine rings joined by a methylene bridge and has a biologic half-life in the body of about 15 days. Thus thiamin-deficient diets will rapidly show effects of thiamin deficiencies.

Riboflavin

Riboflavin participates in oxidation-reduction reactions in numerous metabolic pathways and in energy production via the respiratory chain. Riboflavin is used therapeutically to ameliorate ariboflavinosis resulting from diverse causes such as inadequate dietary intake, decreased assimilation, rare genetic defects in the formation of specific flavoproteins, hormonal disorders and after use of certain drugs.

Niacin

Niacin (nicotinic acid or nicotinamide) is essential in the form of the coenzymes NAD and NADP in which the nicotinamide moiety acts as electron acceptor or hydrogen donor in many biological redox reactions.

Pellagra, the classic niacin deficiency disease, is characterized by symmetrical dermatitis, diarrhea, and dementia. Often associated with a largely cereal diet such as maize or sorghum, the disease is now rarely seen in industrialized countries but still appears in India, China, and Africa. Pellagra often is associated with other micronutrient deficiencies and may develop also in cases of disturbed tryptophan metabolism (carcinoid syndrome, Hartnup's).

Vitamin B6

Vitamin B6 or pyridoxine is involved in the production of ribonucleic acid (RNA) and deoxyribonucleic acid (DNA) and many other reactions in the body. Pyridoxine refers to and includes three different compounds: pyridoxine, pyridoxamine, and pyridoxal.hydrochloride.

Folate

Folate is an essential vitamin that plays a role in the synthesis of RNA, DNA and protein, and thus the folate requirement and, consequently, the risk of deficiency is elevated during periods of rapid growth such as in adolescence. Low folate intakes also are correlated with high levels of serum homocysteine which are associated with an increased risk of atherosclerosis and several forms of vascular disease. Folate is present in many foods, however, the folate content of foods is inherently variable and a large fraction of the folate consumed each day comes from foods that are frequently ingested, but not particularly concentrated, sources of the vitamin. Flour sold in some countries such as USA and Canada is fortified with folic acid.

Vitamin B12

Vitamin B12 or the cobalamins is necessary for overall metabolism, the function of the nervous system, metabolism of folic acid, and the production of red blood cells. There are at least three active forms of cobalamin: cyanocobalamin, hydroxocobalamin, and nitrocobalamin. In a preferred embodiment of the present invention, vitamin B12 is provided in the form of cyanocobalamin.

Pantothenic Acid

Pantothenic acid is important for the production of adrenal gland hormones, increases overall energy, and helps convert food into energy.

Biotin

Biotin, also known as vitamin H and coenzyme R (Hexahydro-2-oxo-1H-thienal[3,4-d]-imidazole-4-pentatonic acid), functions as an essential cofactor for four carboxylases that catalyze the incorporation of cellular bicarbonate into the carbon backbone of organic compounds. Severe deficiencies of biotin can cause thinning of hair, loss of hair color, and eventually complete loss of hair; a scaly, red rash distributed around the openings of the eyes, nose, mouth, and perineal area; and central nervous system abnormalities such as depression, lethargy, hallucinations, and paresthesias.

Administration

The nutritional supplements of the invention may be provided in any suitable dosage form known in the art. For example, the compositions may be incorporated into tablets, powders, granules, beads, chewable lozenges, capsules, aqueous suspensions or solutions, other liquid forms, or similar conventional dosage forms, using conventional equipment and techniques known in the art. Tablet dosage forms are preferred. When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbents, such as silicon dioxide; preservatives, such as methylparaben, propylparaben, and sodium benzoate; surfactants, such as sodium lauryl sulfate, polysorbate 80, and the like; and colorants, such as F.D. & C dyes and the like. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

All of the aforementioned benefits are achieved without wasting vitamin and mineral materials, as characteristic of unitary supplements of the prior art and without the detriment of an excess of some or all of the vitamin and mineral materials. This makes the products of the invention not only more cost effective than conventional supplements, but also, and more significantly, without the detriment of an over dose of any vitamin or mineral materials.

Although the products of the invention are preferably intended for administration to humans, it will be understood that the formulations may also be utilized in veterinary therapies for other animals.

The following example is given to illustrate the invention but is not deemed to be limiting thereof. All amounts specified in the application are based on milligrams unless otherwise indicated. The term "I.U." represents International Units.

EXAMPLES

Example 1

Dose Response Curves

The basic concept underlying the assessment of the most optimum nutrient amounts for a given age group uses the principle of "dose-response curves". At least four groups of individuals were provided with various amounts of a given nutrient and their immune responses were measured using established and accepted techniques. The amount of a nutrient that gave the best response was considered the optimum amount. Dose response curves were determined for all vitamins and trace elements considered essential for human health, particularly immunity.

Data for the dose response curve for zinc in a group of 13–18 year old adolescents is shown in FIGS. 1 and 2, with the total amount of zinc taken is shown for each group. To determine the magnitude of immune response, an aliquot of blood was withdrawn from each subject in the study, blood lymphocytes were separated, washed and mixed with the mitogen phytohemagglutinin (PHA) in previously determined optimum amount. The optimum amount of PHA used in the experiments was predetermined by a set of dose response curves using lymphocytes of a healthy donor and four different concentrations of PHA. After culture in a sterile environment for 72 hours, the cells were washed and mixed with radioactive thymidine. The same steps were undertaken in a control sample in which only the culture medium was used, not PHA. The cells were washed and radioactivity determined.

The ratio of radioactivity in the test samples divided by radioactivity in control samples gave the "stimulation response" shown in FIGS. 1 and 2. Table 1 shows the dose response curve for several immune responses related to dose of zinc in addition to the amount in diet and the maximum response was seen in those receiving a total of 18 mg of zinc.

TABLE 1

Immune response for varying amounts of zinc.

| | Amount of supplemental zinc (mg/day) | | | |
|---|---|---|---|---|
| Immune response | 0 | 11 | 28 | 55 |
| Lymphocyte Response to PHA (stimulation index) | 23 (5) | 77 (8) | 51 (6) | 40 (7) |
| Interleukin-2 (units/ml) | 3 (0.6) | 17 (1.4) | 11 (1.5) | 9 (1.1) |
| Antibody response (median reciprocal titre) | 28 | 254 | 136 | 97 |
| Thymulin activity (median reciprocal titer) | 2 | 114* | 123* | 106* |

Values are shown as median (standard deviation).
For each of the four groups, the average amount of zinc in the diet was 7 mg.
Values for the group receiving 11 mg of zinc supplement are different statistically from other groups.
*Significantly different from the group receiving 0 mg of zinc.

It was concluded from this study that 18 mg of zinc intake produced the best immune response. Dietary intake of zinc was calculated based on three 24-hour recalls and by the food frequency questionnaire methods. The mean of these observations was 7 mg per individual per day. Thus, for the best physiological immune response, an additional 11 mg of zinc would be needed.

Similar experiments were conducted and dose-response curves calculated for each of the other nutrients listed below in Table 2. The optimum amount of each nutrient to maximize immunological response in 13–18 year old adolescents were found to be those amounts set forth in Table 2, with the preferred ranges set forth in Table 3.

Example 2

Randomized Controlled Trial

The most widely accepted ideal method of showing the positive or negative benefits of a treatment modality is the randomized controlled trial (RCT). It can be further refined and made more objective by using the principles of double-blinded observations and placebo-controlled. This implies that a group of study subjects are recruited for the trial. Based on computer-generated random numbers, each individual is assigned to one of the two study groups: "Experimental" who receives the study product, "placebo" who receives the inert or dummy product.

The subjects are observed both clinically and their blood samples are tested periodically. Infection is diagnosed on clinical grounds as also by appropriate laboratory tests on blood, urine, sputum, and by radiographs of the chest, sinuses or other regions, as deemed appropriate for the individual at that time.

The "Experimental" group received the study product, which was made up by mixing together the nutrients in amounts shown in Table 2. The results of the randomized prospective double-blind placebo-controlled trial conducted over a period of 12 months were used to draw conclusions.

From these experiments, it was determined that the supplemental amounts of various vitamins and trace elements, other than what was present in the average diet, that gave the maximum immune response in a group of 13–18 year old adolescents was as set forth in Table 2.

TABLE 2

Optimized supplement formulation for adolescents

| | | |
|---|---|---|
| Calcium | 500 | mg |
| Chromium | 50 | µg |
| Copper | 460 | µg |
| Fluoride | 1.8 | mg |
| Iodine | 100 | µg |
| Iron | 28 | mg |
| Magnesium | 50 | mg |
| Manganese | 3 | mg |
| Molybdenum | 40 | µg |
| Phosphorus | 500 | mg |
| Selenium | 145 | µg |
| Zinc | 11 | mg |
| Beta-carotene | 2.4 | mg |
| Vitamin A | 750 | µg |
| Vitamin C | 75 | mg |
| Vitamin D | 11 | µg |
| Vitamin E | 22 | mg |
| Thiamin | 4.3 | mg |
| Riboflavin | 3.8 | mg |
| Niacin | 19 | mg |
| Vitamin B6 | 2.9 | mg |
| Folate | 400 | µg |
| Vitamin B12 | 4.7 | µg |

TABLE 2-continued

Optimized supplement formulation for adolescents

| | |
|---|---|
| Pantothenic acid | 2.0 mg |
| Biotin | 20 µg |

The amounts of nutrients expected to give physiologically similar results are recognized to be + or −15% of the specified value. Thus, the preferred range of nutrient amounts that would give the response as noted in Table 2 is set forth in Table 3 below.

TABLE 3

Preferred range of values for inventive supplement

| | |
|---|---|
| Calcium | 425–575 mg |
| Chromium | 42.5–57.5 mg |
| Copper | 391–529 µg |
| Fluoride | 1.53–2.07 mg |
| Iodine | 85–115 µg |
| Iron | 23.8–32.2 mg |
| Magnesium | 42.5–57.5 mg |
| Manganese | 2.65–3.45 mg |
| Molybdenum | 34–46 µg |
| Phosphorus | 425–575 mg |
| Selenium | 123.25–166.75 µg |
| Zinc | 9.35–12.65 mg |
| Beta-carotene | 2.04–2.76 mg |
| Vitamin A | 637.5–862.5 µg |
| Vitamin C | 63.75–86.25 mg |
| Vitamin D | 9.35–12.65 µg |
| Vitamin E | 18.7–25.3 mg |
| Thiamin | 3.65–4.95 mg |
| Riboflavin | 3.23–4.37 mg |
| Niacin | 16.15–21.85 mg |
| Vitamin B6 | 2.46–3.34 mg |
| Folate | 340–460 µg |
| Vitamin B12 | 3.99–5.41 µg |
| Pantothenic acid | 1.7–2.3 mg |
| Biotin | 17–23 µg |

Example 3

Nutritional Deficiencies

The prevalence of various nutrient deficiencies was also studied for the control group and for the group receiving the various levels of supplementation. The prevalence of nutrient deficiencies at the base line for all groups undertaking the study is shown in Table 4 below. It was similar and statistically not significantly different in the two groups at the base line. However, there was an almost complete elimination of nutritional deficiencies in the group given the multinutrient, whereas no change occurred in the placebo group.

TABLE 4

Prevalence of nutritional deficiencies.

| Nutrient | Prevalence of deficiency (%) |
|---|---|
| Calcium | 14.6 |
| Chromium | 4.2 |
| Copper | 0 |
| Fluoride | 0 |
| Iodine | 4.2 |
| Iron | 31.3 |
| Magnesium | 4.2 |
| Molybdenum | 6.3 |
| Phosphorus | 4.2 |

TABLE 4-continued

Prevalence of nutritional deficiencies.

| Nutrient | Prevalence of deficiency (%) |
|---|---|
| Selenium | 10.4 |
| Zinc | 16.7 |
| Beta-carotene | 14.6 |
| Vitamin A | 2.1 |
| Vitamin C | 10.4 |
| Vitamin D | 14.6 |
| Vitamin E | 8.3 |
| Thiamin | 4.2 |
| Riboflavin | 4.2 |
| Niacin | 6.3 |
| Vitamin B6 | 10.4 |
| Folate | 6.3 |
| Vitamin B12 | 0 |
| Pantothenic acid | 0 |
| Biotin | 2.1 |

Example 4

Immune Responses and Infection-related Morbidity

A study was also conducted to compare the immune responses of the control group and for the group receiving the various levels of supplementation. Immune responses were comparable in the two groups at base line. However, the adolescents given the multinutrient showed a much higher response in all the parameters tested (Table 5) including the number of T lymphocytes, CD4+ helper T cells, lymphocyte response to mitogen PHA, interleukin-2 production by mitogen-stimulated lymphocytes, antibody production after booster injection of tetanus toxoid, and natural killer cell activity.

Infection rate was determined meticulously and showed a significant reduction in the group receiving the multinutrient as shown in Table 5 below.

TABLE 5

Immune responses of supplement group and control group.

| Parameter | Multinutrient Group | Placebo Control | p |
|---|---|---|---|
| T lymphocytes % | 68.3 (2.7) | 57.4 (3.0) | <0.01 |
| CD4 + T cells % | 49.6 (2.5) | 43.1 (2.1) | <0.01 |
| Lymphocyte Stimulation response | 79.2 (11.2) | 48.5 (7.8) | <0.05 |
| Interleukin-2 U/ml | 11.2 (0.8) | 7.3 (1.0) | <0.01 |
| Antibody response To tetanus toxoid Mean titre | 874 | 541 | <0.01 |
| Natural killer Cell activity % | 47.4 (4.3) | 37.8 (5.1) | <0.05 |
| Infection Days per year | 11.1 (2.5) | 17.9 (2.6) | <0.01 |

The data presented in this document show that the administration daily of a multinutrient designed to meet the unique requirements of adolescents enhances immune responses and reduces infection in this age group.

The invention being thus described, it will be obvious that the same may be varied in many ways. Such variations are not to be regarded as a departure from the spirit and scope of the invention and all such modifications are intended to be included within the scope of the following claims.

I claim:

1. A nutritional supplement for adolescents for improving the immunological status of adolescents, said nutritional supplement comprising:

Calcium in the amount of about 425 to about 575 mg;
Chromium in the amount of about 42.5 to about 57.5 µg;
Copper in the amount of about 391 to about 529 µg;
Fluoride in the amount of about 1.53 to about 2.07 mg;
Iodine in the amount of about 85 to about 115 µg;
Iron in the amount of about 23.8 to about 32.2 mg;
Magnesium in the amount of about 42.5 to about 57.5 mg;
Manganese in the amount of about 2.65 to about 3.45 mg;
Molybdenum in the amount of about 34 to about 46 µg;
Phosphorus in the amount of about 425 to about 575 mg;
Selenium in the amount of about 123.25 to about 166.75 µg;
Zinc in the amount of about 9.35 to about 12.65 mg;
Beta-carotene in the amount of about 2.04 to about 2.76 mg;
Vitamin A in the amount of about 637.5 to about 862.5 µg;
Vitamin C in the amount of about 63.75 to about 86.25 mg;
Vitamin D in the amount of about 9.35 to about 12.65 µg;
Vitamin E in the amount of about 18.7 to about 25.3 mg;
Thiamin in the amount of about 3.65 to about 4.95 mg;
Riboflavin in the amount of about 3.23 to about 4.37 mg;
Niacin in the amount of about 16.15 to about 21.85 mg;
Vitamin B6 in the amount of about 2.46 to about 3.34 mg;
Folate in the amount of about 340 to about 460 µg;
Vitamin B12 in the amount of about 3.99 to about 5.41 µg;
Pantothenic acid in the amount of about 1.7 to about 2.3 mg; and
Biotin in the amount of about 17 to about 23 µg.

2. The nutritional supplement of claim 1 wherein said supplement comprises:
Calcium in the amount of about 500 mg;
Chromium in the amount of about 50 µg;
Copper in the amount of about 460 µg;
Fluoride in the amount of about 1.8 mg;
Iodine in the amount of about 100 µg;
Iron in the amount of about 28 mg;
Magnesium in the amount of about 50 mg;
Manganese in the amount of about 3 mg;
Molybdenum in the amount of about 40 µg;
Phosphorus in the amount of about 500 mg;
Selenium in the amount of about 145 µg;
Zinc in the amount of about 11 mg;
Beta-carotene in the amount of about 2.4 mg;
Vitamin A in the amount of about 750 µg;
Vitamin C in the amount of about 75 mg;
Vitamin D in the amount of about 11 µg;
Vitamin E in the amount of about 22 mg;
Thiamin in the amount of about 4.3 mg;
Riboflavin in the amount of about 3.8 mg;
Niacin in the amount of about 19 mg;
Vitamin B6 in the amount of about 2.9 mg;
Folate in the amount of about 400 µg;
Vitamin B12 in the amount of about 4.7 µg;
Pantothenic acid in the amount of about 2.0 mg; and
Biotin in the amount of about 20 µg.

3. A method for maintaining optimal health of an adolescent in need thereof, comprising administering the supplement of claim 1.

4. A method for improving the immunological status of adolescents, said method comprising administering a nutritional supplement comprising:
Calcium in the amount of about 425 to about 575 mg;
Chromium in the amount of about 42.5 to about 57.5 µg;
Copper in the amount of about 391 to about 529 µg;
Fluoride in the amount of about 1.53 to about 2.07 mg;
Iodine in the amount of about 85 to about 115 µg;
Iron in the amount of about 23.8 to about 32.2 mg;
Magnesium in the amount of about 42.5 to about 57.5 mg;
Manganese in the amount of about 2.65 to about 3.45 mg;
Molybdenum in the amount of about 34 to about 46 µg;
Phosphorus in the amount of about 425 to about 575 mg;
Selenium in the amount of about 123.25 to about 166.75 µg;
Zinc in the amount of about 9.35 to about 12.65 mg;
Beta-carotene in the amount of about 2.04 to about 2.76 mg;
Vitamin A in the amount of about 637.5 to about 862.5 µg;
Vitamin C in the amount of about 63.75 to about 86.25 mg;
Vitamin D in the amount of about 9.35 to about 12.65 µg;
Vitamin E in the amount of about 18.7 to about 25.3 mg;
Thiamin in the amount of about 3.65 to about 4.95 mg;
Riboflavin in the amount of about 3.23 to about 4.37 mg;
Niacin in the amount of about 16.15 to about 21.85 mg;
Vitamin B6 in the amount of about 2.46 to about 3.34 mg;
Folate in the amount of about 340 to about 460 µg;
Vitamin B12 in the amount of about 3.99 to about 5.41 µg;
Pantothenic acid in the amount of about 1.7 to about 2.3 mg; and
Biotin in the amount of about 17 to about 23 µg.

5. The method of claim 4 wherein said supplement comprises:
Calcium in the amount of about 500 mg;
Chromium in the amount of about 50 µg;
Copper in the amount of about 460 µg;
Fluoride in the amount of about 1.8 mg;
Iodine in the amount of about 100 µg;
Iron in the amount of about 28 mg;
Magnesium in the amount of about 50 mg;
Manganese in the amount of about 3 mg;
Molybdenum in the amount of about 40 µg;
Phosphorus in the amount of about 500 mg;
Selenium in the amount of about 145 µg;
Zinc in the amount of about 11 mg;
Beta-carotene in the amount of about 2.4 mg;
Vitamin A in the amount of about 750 µg;
Vitamin C in the amount of about 75 mg;
Vitamin D in the amount of about 11 µg;
Vitamin E in the amount of about 22 mg;
Thiamin in the amount of about 4.3 mg;
Riboflavin in the amount of about 3.8 mg;
Niacin in the amount of about 19 mg;
Vitamin B6 in the amount of about 2.9 mg;
Folate in the amount of about 400 µg;
Vitamin B12 in the amount of about 4.7 µg;
Pantothenic acid in the amount of about 2.0 mg; and
Biotin in the amount of about 20 µg.

* * * * *